US007043056B2

(12) United States Patent
Edwards et al.

(10) Patent No.: US 7,043,056 B2
(45) Date of Patent: May 9, 2006

(54) FACIAL IMAGE PROCESSING SYSTEM

(75) Inventors: Timothy Edwards, Braddon (AU); Jochen Heinzmann, Kaleen (AU); Sebastien Rougeaux, Turner (AU); Alex Zelinsky, O'Connor (AU)

(73) Assignee: Seeing Machines Pty Ltd, (AU)

( * ) Notice: Subject to any disclaimer, the term of this patent is extended or adjusted under 35 U.S.C. 154(b) by 452 days.

(21) Appl. No.: 10/350,835

(22) Filed: Jan. 24, 2003

(65) Prior Publication Data
US 2003/0169907 A1 Sep. 11, 2003

Related U.S. Application Data

(63) Continuation of application No. PCT/AU01/00249, filed on Mar. 8, 2001.

(51) Int. Cl.
G06K 9/00 (2006.01)

(52) U.S. Cl. ...................................... 382/103; 382/118
(58) Field of Classification Search ................ 382/103, 382/104, 117, 118, 154, 199; 348/77, 78; 340/575, 576, 573.7
See application file for complete search history.

(56) References Cited

U.S. PATENT DOCUMENTS

| | | | | |
|---|---|---|---|---|
| 5,786,765 A | * | 7/1998 | Kumakura et al. | 340/576 |
| 5,802,220 A | | 9/1998 | Black et al. | 382/276 |
| 5,878,156 A | * | 3/1999 | Okumura | 382/118 |
| 5,933,527 A | | 8/1999 | Ishikawa | 382/190 |
| 6,009,210 A | | 12/1999 | Kang | 382/276 |
| 6,031,539 A | | 2/2000 | Kang et al. | 345/419 |
| 6,049,747 A | * | 4/2000 | Nakajima et al. | 701/45 |
| 6,091,334 A | * | 7/2000 | Galiana et al. | 340/576 |
| 6,094,498 A | | 7/2000 | Okumura | 382/118 |
| 6,097,295 A | * | 8/2000 | Griesinger et al. | 340/576 |
| 6,144,755 A | * | 11/2000 | Niyogi et al. | 382/118 |
| 6,243,015 B1 | * | 6/2001 | Yeo | 340/576 |

FOREIGN PATENT DOCUMENTS

| | | |
|---|---|---|
| EP | 0 990 416 A1 | 4/2000 |
| WO | WO 99/64961 A1 | 12/1999 |
| WO | WO 01/22872 A2 | 4/2001 |

OTHER PUBLICATIONS

Ueno et al., "Development of Drowsiness Detection System," *Proc. Vehicle Navigation & Information Systems Conf.*, Aug./Sep. 1994, pp. 15-20.*

Heinzmann et al., "3-D Facial Pose and Gaze Point Estimation using a Robust Real-Time Tracking Paradigm," *Proc. Int. Conf. on Automatic Face and Gesture Recognition*, Apr. 1998, pp. 142-147.*

(Continued)

*Primary Examiner*—Andrew W. Johns
(74) *Attorney, Agent, or Firm*—St. Onge Steward Johnston & Reens, LLC

(57) ABSTRACT

A method of determining an eye gaze direction of an observer is disclosed comprising the steps of: (a) capturing at least one image of the observer and determining a head pose angle of the observer; (b) utilizing the head pose angle to locate an expected eye position of the observer, and (c) analyzing the expected eye position to locate at least one eye of the observer and observing the location of the eye to determine the gaze direction.

26 Claims, 6 Drawing Sheets

OTHER PUBLICATIONS

Ko et al., "Facial Feature Tracking for Eye-Head Controlled Human Computer Interface," *Proc. IEEE Region 10 Conf.*, Sep. 1999, pp. 72-75.*

Matsumoto et al., "Reat-time Stereo Face Tracking System for Visual Human Interface," *Proc. Int. Wksp. on Recognition, Analysis, and Tracking of Face and Gestures in Real-Time Systems*, Sep. 1999, pp. 77-82.*

Matsumoto et al., "Real-time Face Tracking System for Human-Robot Interaction," *Proc. Int. Conf. on Systems, Man, and Cybernetics*, vol. II, Oct. 1999, pp. 830-835.*

Matsumoto et al., "An Algorithm for Real-time Stereo Vision Implementation of Head Pose and Gaze Direction Measurement," *Proc. Int. Conf. on Automatic Face and Gesture Recognition*, Mar. 2000, pp. 499-504.*

Chen et al., "Head pose estimation using both color and feature information," *Proc. Int. Conf. on Pattern Recognition*, vol. 2, Sep. 2000, pp. 842-845.*

Jie Yang, Rainer Stiefelhagen, Uwe Meier and Alex Waibel, "Real-time Face and Facial Feature Tracking and Application," Proc. AVSP'98, pp. 79-84, 1998.

Rainer Stiefelhagen, Jie Yang and Alex Waubel, "A Model-Based Gaze Tracking System" 1996, pp. 304-310, IEEE Joint Symp. on Intelligence and Systems.

Thanarat Horprasert, Yaser Yacoob and Larry S. Davis, "Computing 3-D orientation from a monocular image sequence" 1997, pp. 244-252, Proc. SPIE vol. 2962.

* cited by examiner

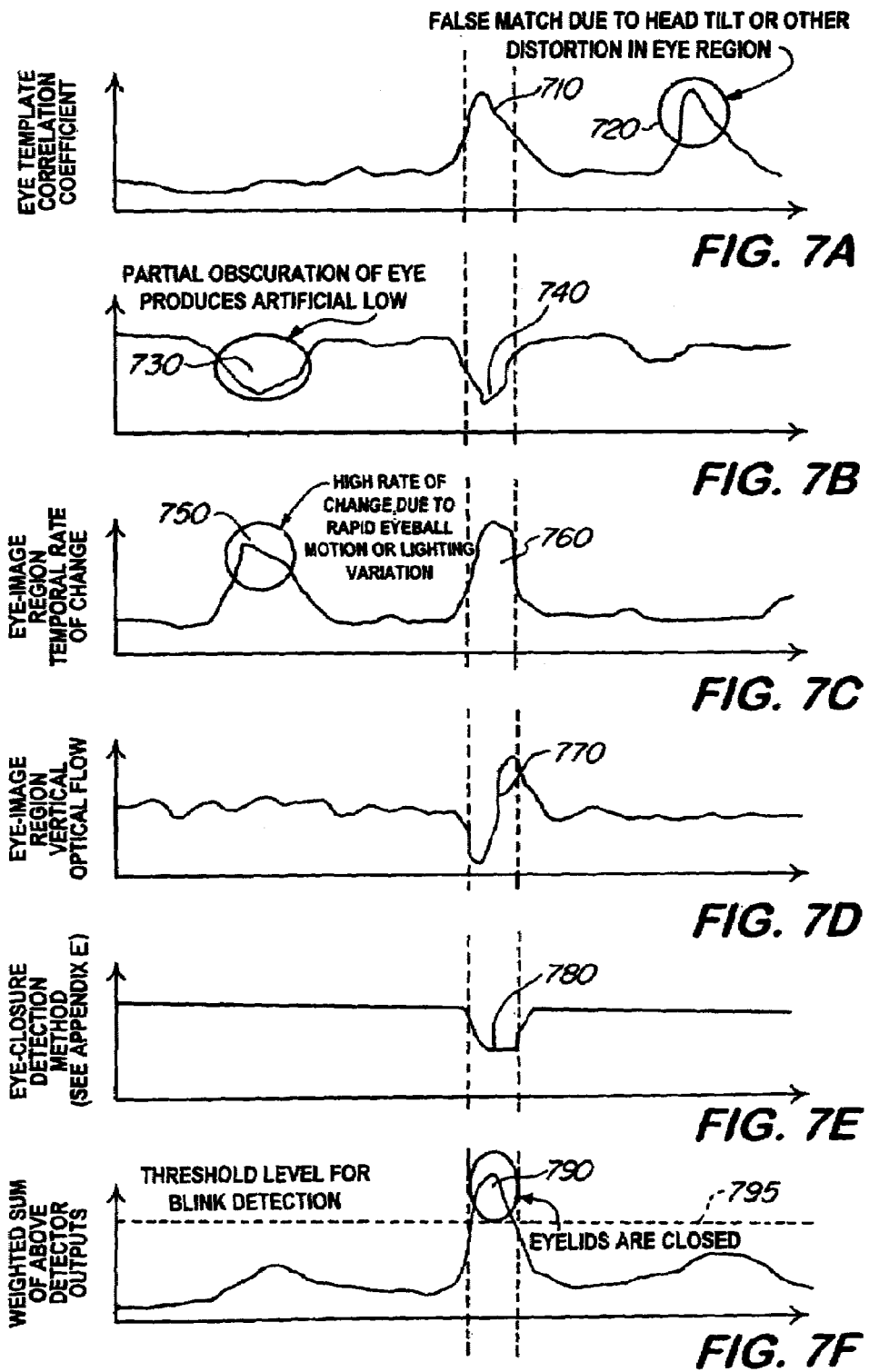

FACIAL IMAGE PROCESSING SYSTEM

This application is a continuation of PCT application Ser. No. PCT/AU01/00249 filed Mar. 8, 2001, which claims the benefit of the filing date of Australian Application No. PQ8960 filed Jul. 24, 2000.

FIELD OF THE INVENTION

The present invention relates to a system and method for determining three dimensional head pose, eye gaze direction, eye closure amount, blink detection and flexible feature detection on the human face using image analysis from multiple video sources. Additionally, the invention relates to systems and methods that makes decisions using passive video analysis of a human head and face. These methods can be used in areas of application such as human-performance measurement, operator monitoring and interactive multimedia.

BACKGROUND OF THE INVENTION

Early techniques for determining head-pose used devices that were fixed to the head of the subject to be tracked. For example, reflective devices were attached to the subjects head and using a light source to illuminate the reflectors, the reflector locations were determined. As such reflective devices are more easily tracked than the head itself, the problem of tracking head-pose was simplified greatly.

Virtual-reality headsets are another example of the subject wearing a device for the purpose of head-pose tracking. These devices typically rely on a directional antenna and radio-frequency sources, or directional magnetic measurement to determine head-pose.

Wearing a device of any sort is clearly a disadvantage, as the user's competence and acceptance to wearing the device then directly effects the reliability of the system. Devices are generally intrusive and will affect a user's behaviour, preventing natural motion or operation.

Structured light techniques that project patterns of light onto the face in order to determine head-pose are also known.

The light patterns are structured to facilitate the recovery of 3D information using simple image processing. However, the technique is prone to error in conditions of lighting variation and is therefore unsuitable for use under natural lighting conditions.

U.S. Pat. No. 6,049,747 describes a driver-monitoring device that determines head-pose using structured infra-red light. The technique measures head-pose and assumes it is an estimate of the driver's gaze direction. The lack of a more detailed gaze analysis clearly limits the usefulness of such a system.

Another group of head-pose tracking techniques are the so called "Classification techniques". Classification techniques attempt to classify a video image as one of a set of possible outcomes. The techniques often use methods such as histograms, principal component analysis and template matching. The main problem with the approach is that only head orientation can be measured—head translation is not accounted for.

Head orientation is measured by classifying the instant orientation as one of finite set of possible orientations. As the number of candidate head positions is increases, so does the probability of false classification. Another difficulty is that the set of candidate head positions must be generated in advance. This is a laborious process.

The system presented by Pappu and Beardsley in "A Qualitative Approach to Classifying Gaze Direction", Conference of Automatic and Gesture Recognition 1998, Nara Japan, provides an example of the present state of classification techniques for use in head-pose determination.

Other known systems of head-pose detection use techniques that rely on fitting a generic 3D head-mesh structure to sequences of images. This involves iteratively refining an estimation of the head-pose through measurement of the error between candidate 2D projections of the 3D mesh, and the image.

The technique is computationally expensive, and the accuracy is largely dependent on the similarity between the generic mesh model and the actual head being tracked. The wide variety of human face structure thus prevents any guaranteed measure of accuracy. The technique is likely to be applied for non-real-time image processing, with the aim of altering the appearance of a person's face.

Examples of systems that use this style of technique can be seen in "A Robust Model-Based Approach for 3D Head Tracking in Video Sequences" by Marius Malciu and Francoise Preteux, and "Robust 3D Head Tracking Under Partial Occlusion" by Ye Zhang and Chandra Kambhamettu, both from Conference of Automatic and Gesture Recognition 2000, Grenoble France.

An further known technique which may be used for head-pose detection is the structure from motion technique. Structure from motion is a technique whereby the three-dimensional geometry of an object can be recovered from a single video source, using the information available from different views of the object as it moves relative to the camera. Such a technique is discussed in "Real Time Tracking and Modelling of Faces: An EKF-based Analysis by Synthesis Approach" in Proceedings of the Modelling People Workshop at the International Conference on Computer Vision, 1999 by J. Strom, T. Jebara, S. Basu and A. Pentland.

When used for head-pose tracking, a 3D model of the head is initialised using a generic three-dimensional mesh, and an extended Kalman filter is used to iteratively refine both the facial geometry and the head-pose.

Convergence of this technique is not assured due to the typical variation of human facial geometry. This is a similar problem to the Template Mesh Model Fitting technique, though a little lessened due to the adaptive approach used.

It is also important to note that the technique is fragile to facial deformations such as smiling and blinking.

Fatigue measurement using blink detection is described in U.S. Pat. No. 5,867,587 and U.S. Pat. No. 5,878,156 describes a technique for fatigue measurement based on detecting the state of the eyes. Both methods are fragile if applied to tasks that involve wide ranging head motions, such as when driving a car.

Stereo reconstruction using feature templates is also known. Ming XU and Takao Akatsuka in "Detecting Head Pose from Stereo Image Sequence for Active Face Recognition" from Conference on Automatic Face and Gesture Recognition 1998, Nara Japan, present a system for active face recognition. The system uses only four facial features, two of which are the eyes, to recover and approximate head-pose. The system cannot be used for practical head-pose tracking as it is fragile to head and eye motion (including blinking), and requires the image background to be uniform. The range and accuracy of head-motion measurement is also very limited due to the deformation and/or occlusion of features as the head is moved.

Work by Norbert Kruger, Michael Potzsch, Thomas Maurer and Michael Rinne in "Estimation of Face Position and Pose with Labelled Graphs" from Proceedings of British Machine Vision Conference, 1996, investigates the use of Gabor filter based template tracking combined with bunched graph fitting. This is an early paper, and further work can be seen at the Internet address:

http://selforg.usc.edu:8376/~tmaurer/introduction.html

However the system described has no facility for using the head-pose information to reliably track eye-gaze.

Similarly to head-pose detection, eye-gaze direction measurement has, in the past, been achieved with the use of devices worn by the subject.

Devices worn to detect eye-gaze direction have included mirrors, lenses, or cameras placed near the eye or in some instances special contact lenses to be placed on the eye. All the methods aim to obtain high-resolution or easily identifiable images of the eye that are independent of head-position.

Again, as for head-pose direction, wearing a device of any sort is a disadvantage, as the user's competence and acceptance to wearing the device then directly effects the reliability. Devices are generally intrusive and will affect a user's behaviour, interfering with natural motion and operation.

The infra-red technique involves shining an infra-red light on the face of the person being monitored then detecting and analysing the reflections from the person's eyes.

Infra-red reflection techniques operate by detecting either the reflection from the eye surface, or cornea of the eye, or both.

The first reflection is from the spherical eye surface. This reflection determines the position of the eye. If the video camera is collocated with the source of the infra-red, the position of the reflection directly measures the position of the eyeball centre. The cornea, on the other hand, acts as a corner reflector.

Image processing is used to detect reflections from the eye surface or cornea, and to localise the centre of the limbus. An accurate gaze estimate can then be computed using the relative position difference between the iris centre and the reflections.

Infra-red sensing can yield very precise eye-gaze measurement. However, the technique is limited for the following reasons:

The cornea can only reflect light back to a source (act as a corner reflector) over a small range of angles. This limits the use of infra-red to applications where gaze is restricted to a small area.

To reliably analyse the reflections on the eye, a high-resolution image is required. Due to finite image sensor resolution, this limits the possible field-of-view for the sensor. To overcome this problem, either a very expensive high-resolution sensor must be used, or a bulky and failure-prone mechanical pan-tilt mechanism can be employed.

Natural lighting conditions can easily confuse the reflection detection process. Flashing techniques are often used to improve reliability, however saturation of the pupil with sunlight will cause a flashing detector to fail. Fluctuating light on the pupil, typical of driving conditions, will also produce erroneous measurements.

The eye-gaze measurements taken using the infra-red reflection technique are in two dimensions only. That is, because the distance of the eyeball from the camera is not determined, the measurement is based on the assumption that the head remains at a fixed distance from the camera Motion of the head towards or away from the camera will change the distance between the eye-reflections, and may be interpreted as a change in gaze-direction.

Techniques to compensate for motion toward or away from the camera are based on measuring the image area of the reflections or other regions on the face, and are prone to noise due to resolution constraints, overlapping reflections from other light sources, and distortion introduced by rotation of the head.

The majority of the known techniques for passive eye-gaze analysis suffer from one of the number of common drawbacks, including the following:

The eye-gaze direction is assumed to be perpendicular to the orientation of the face; the technique is only an eye region detection technique. Passive eye-gaze analysis is not actually performed.

The technique performs eye-gaze tracking without three-dimensional head-pose tracking to compensate for head orientation and motion, thus limiting the application of the technique to strict translations in the image plane, or no head-motion at all.

Some known techniques use 'neural-networks to estimate gaze direction. Neural networks require long training sequences for every person to be monitored, and do not allow for any head motion.

The techniques based on finding the distortion of the iris circle due to eye rotation tend to be extremely noise and resolution sensitive.

The technique used to find the iris in "Vision-Based Eye-Gaze Tracking for Human Computer Interface", IEEE International Conference on Systems, Man and Cybernetics, Tokyo, Japan, 1999 by Kim Kyung-Nam et. al, uses a circular Hough transform to find the iris centre. The gaze direction is determined using the distance of the iris centre from a fixed marker that must be worn on the face. Thus, head rotation or head translation along the camera axis will be interpreted by the technique as a change in gaze direction.

U.S. Pat. No. 6,072,892 describes an "eye position detecting apparatus and method therefor". The technique locates the position of the eyes in an image of a face using a histogram classification approach. The technique only locates the eyes, and does not perform any actual eye-gaze measurement.

U.S. Pat. No.6,055,323 describes a technique for "face image processing" by locating the position of the eyes in an image of a face by first locating nares (nostrils) and then using a default model of the face to determine the eye image regions.

U.S. Pat. No. 5,859,686 describes an "eye finding and tracking system" which locates and tracks the eyes using normalised cross-correlation of iris image templates, combined with knowledge of probable eye-positions to reduce the probability of erroneous detection.

Each of the above techniques fails to account for three-dimensional motion of the head, and are prone to error due to head-rotation and head-translation along the camera axis.

Device wearing and active sensing are also used to detect eye closure and blinking.

Devices worn to measure eye-closure or detect blinking fall into two categories, namely, techniques using electrodes worn near the eyes that measure eyelid muscle activity, and devices worn on the head that project infra-red light onto the eye region, and determine eye-closure based on the amount of reflected light.

Clearly wearing a device of any sort is a disadvantage, as the user's competence and acceptance to wearing the device then directly effects the reliability. Devices are generally intrusive and will affect a user's behaviour, interfering with natural motion and operation.

One known passive video technique used for eye closure and blink detection fits deformable eye templates to three parameters. The first two parameters represent the parabolic shapes of the eyelids, and the third represents the radius of a circle representing the edge between the iris and sclera The technique relies on determining the location of the corners of each eye. Similarly to the techniques for eye finding, there is the in-built assumption that the head does not rotate away from the image plane, because the head-pose is not tracked in three dimensions.

U.S. Pat. No.5,867,587 describes an "impaired operator detection and warning system employing eyeblink analysis". The technique detects blink events, and measures blink duration with the aim of detecting a fatigued operator. The eyes are first found using the patented technique of U.S. Pat. No. 5,859,686. Blink events are detected when a fluctuation in the eye-template correlation meets specific set of requirements. The blink technique described is defective in situations where an operator's head rotates significantly, due to the inadequate head-pose tracking.

U.S. Pat. No. 5,878,156 describes a technique for "detecting the open/closed state of the eyes based on analysis of relation between eye and eyebrow images in input face images". The technique binarizes the images regions surrounding the eye and eyebrow, determines which regions represent the eye and eyebrow, then calculates the distance between the centroids of these regions. A technique that determines the ratio of the areas of the eye and eyebrow image regions is used to add robustness to variation in head-pose distance from the camera This technique may be unreliable when the head is rotated left and right, as rotational motion of the head in this plane will cause the eyebrow and eye image-region area-ratio to change which will be interpreted as a change in head-pose distance. The technique will also be unreliable when used on operators with fair or blonde eyebrows, when the eyebrows are moved around on the face, or when reflected light conditions on the eye change. Additionally, the technique will not work at all when using glasses or sunglasses, at the very least due to the fact that the frames will cover the eyebrow image regions.

In, summary the known techniques for eye-gaze measurement, eye-closure measurement, blink detection have failed to use a three-dimensional estimate of head-pose as the foundation for further facial analysis, such as eye-gaze, closure or blink detection. The techniques have measured head-pose, eye-gaze, eye-closure or blink detection, individually, but not simultaneously. Thus, the techniques have failed to take advantage of the relationships between the measures, and, in general, are limited in their application due to over-simplified approaches to the measurement problem.

More specifically, the known techniques have not suitably accounted for large variations in head position and rotation when measuring eye-gaze, eye-closure or blink event detection, and thus although claiming to be robust, are only robust given specific restrictions on head-pose. Thus the known techniques remain fragile when applied to head motions typical of operating a machine in a seated position, such as driving a car.

Additionally, no prior technique is known that automatically detects which parts of the face are flexible. There is a need for such a technique in the area of motion capture for facial animation.

Present day facial animation systems map defined points or nodes on the face of a human, onto another set of points or nodes on the face of a computer-animated character. These points are selected manually by placing markers on the face, and then placing corresponding control points onto the face geometry in the animation software. This process of identifying control points is lengthy and would be improved by automatically finding all the flexible points on the face.

U.S. Pat. No. 6,028,960 describes a technique for "face feature analysis for automatic lip-reading and character animation". The technique tracks the face by identifying the nostril features, and then determining lip and mouth contours. The lip and mouth contours are then used to control an artificial face model. The technique simplifies the process of animating lip-motion for computer-animated talking characters. However, the technique makes no mention of using any other facial feature other than the lips to perform this animation. It instead relies on the artificial generation of face structure using only the lip and mouth contours. It does not simplify the animation process for capturing facial expressions that involve eyelid, eyeball, eyebrow and other facial expressions not involving the mouth.

As the technique only tracks the nostrils, it will only be so while the nostrils are visible to the camera Clearly the system will fail for head orientations where the head is tilted forward so that the nostrils are obscured from the camera by the top of the nose.

U.S. Pat. No. 6,016,148 describes a technique for "automated mapping of facial images to animation wireframes topologies". The technique describes the general principle of using measured positions of points or nodes on the face to alter corresponding points or nodes on a computer modelled wire-frame mesh topology. The patent does not include a method to automatically determine the location of these points or nodes on the face.

SUMMARY OF THE INVENTION

It is an object of the present invention to provide an improved system and method for determining head pose.

In accordance with a first aspect of the present invention, there is provided a method of passively determining the direction of eye gaze of a person, the method including the steps of: capturing images of the face and head of the person from at least two viewpoints; localising the face within two or more of the captured images; computing an initial estimate of head-pose, identifying feature search regions, based on the initial estimate of head pose, within each captured image that may contain an identifiable facial feature; measuring the position of two or more facial features within two or more respective feature search regions in each of the captured images; computing the three-dimensional location of each of the two or more facial features; determining a head pose measurement, the head pose measurement including a rotational displacement and translation displacement which best match a head-model to the computed location of the two or more facial features; using the head pose measurement to determine the location the centre of one eyeball; using the head pose measurement to find an eye region corresponding with the eyeball, within each captured image, and determining the location of the centre of the iris of the eye; using the determined position of the centre of the eyeball and the determined location of the centre of the iris of the eye, to calculate an eye-gaze direction for the eye.

In accordance with a further aspect of the present invention, there is provided a method of passively determining the direction of eye gaze of a person, wherein the direction of eye gaze of the person is calculated by averaging the direction of eye gaze of the person's two eyes, wherein the direction of eye gaze for each eye is determined using the method aforementioned.

In accordance with a further aspect of the present invention, there is provided a method of determining the eye closure amount of an eye located on a person's face, the eye having an eyeball, a top eyelid, and a bottom eyelid, the top and bottom eyelids meeting at a pair of eye corners; wherein eye closure amount is defined as the ratio of eye corner separation to eyelid distance, including the steps of: capturing images of the face and head of the person from at least two viewpoints; determining a head pose measurement, from the captured images; using the head pose measurement to determine an eye region within the captured image; determining the location of the eye corners within the eye region; fitting at least two oriented edge detectors to the top eyelid and to the bottom eyelid, such that one of the oriented edge detectors of the top eyelid intersects with one oriented edge detectors of the bottom eyelid at each eye corner; approximating the position of the top eyelid, and the bottom eyelid, by fitting a parabola to the at least two oriented edge detectors corresponding to each eyelid, such that each parabola is tangential to the at least two oriented edge detectors of the parabola's respective eyelid; determining the eye corner separation by calculating the distance between the eye corners determining the maximum eyelid distance by calculating the maximum distance between the parabolas on the portion of the parabolas between the eye corners, in a direction perpendicular to a line joining the eye corners; calculating the eye closure amount by taking the ratio of the determined eye corner separation to maximum eyelid distance.

In accordance with a further aspect of the present invention, there is provided a method of detecting a blink of a person's eye, the method including the following steps: calculating eye closure value using ; forming a temporal sequence of eye closure values; and comparing the temporal sequence of eye closure values with a blink template, wherein the blink template can comprise a sequence of eye closure values corresponding to blink, in order to determine a correlation value between the blink template and the model temporal sequence of eye closure value, wherein a blink can be determined to have occurred if the correlation value can be greater than a predetermined threshold.

In accordance with a further aspect of the present invention, there is provided a method of detecting a blink of a person's eye using a plurality of independent measurements, wherein each of the plurality of measurements produces a time varying output value, and at least one of the plurality of measurements can be, the method including the step of: combining the output value of two or more of the plurality of independent measurements in a weighted manner to calculate a blink detection value, wherein a blink can be determined to have occurred if the blink detection value can be greater than a predetermined threshold blink detection value. At least one of measurements can be selected from: an eye region template correlation coefficient; an optical flow measurement in the eye region; eye region image rate of change; colour segmentation within the eye region; and iris template correlation coefficient.

In accordance with a further aspect of the present invention, there is provided a method of determining an eye gaze direction of an observer comprising the steps of: (a) capturing at least one image of the observer and determining a head pose angle of the observer; (b) utilising the head pose angle to locate an expected eye position of the observer; and (c) analysing the expected eye position to locate at least one eye of the observer and observing the location of the eye to determine an eye gaze direction.

The step (a) preferably can include capturing an image in stereo and processing the image in stereo. The step can also further include (i) determining a set of distinguishable feature locations on an observer's face; and (ii) sorting candidate feature locations of a current head pose to determine a likely head pose.

The method preferably degrades gracefully in the presence of occlusion of the observer's face such as by the wearing of sunglasses by a user.

The method also further preferably includes determining the three dimensional position of a centre of rotation of an observer's eye and determining eye closure and blinking.

The method utilises a measure feature location to determine if individual features on an observer's face are preferably flexible or fixed.

According to a further aspect of the present invention there is provided a method of detecting a flexible feature on a person's face, said method including the step of comparing the variance of said feature's position from an expected position of said facial feature, based on a head-pose measurement, with a threshold variance to determine whether the feature is flexible. Preferably a head-pose measurement is determined using the method described above.

According to a further aspect of the present invention there is provided a method of analysis of a person performing a task wherein the method of any one of the previous claims is used to analyse an action of said subject.

According to a further aspect of the present invention there is provided a method of animating an image, wherein the movement of a subject is tracked using a method according to any one of the previous claims, and wherein said image is animated in response to said movement.

According to a further aspect of the present invention there is provided a method for measuring operator fatigue including the step of:
  tracking any one or more of: head-pose; eye gaze; eye closure amount; or blink rate of the operator.

It is preferable that any one or more of the parameters of head-pose; eye gaze; eye closure amount; or blink rate is measured using a method described above.

Various apparatus for implementing the above methods are also disclosed.

BRIEF DESCRIPTION OF THE DRAWINGS

Notwithstanding any other forms which may fall within the scope of the present invention, preferred forms of the invention will now be described by way of example only with reference to the accompanying drawings in which:

FIG. 7 shows a series of graphs for the multi-modal analysis eye-blink according to an embodiment of the invention.

DETAILED DESCRIPTION OF THE EMBODIMENT

Figure 1:
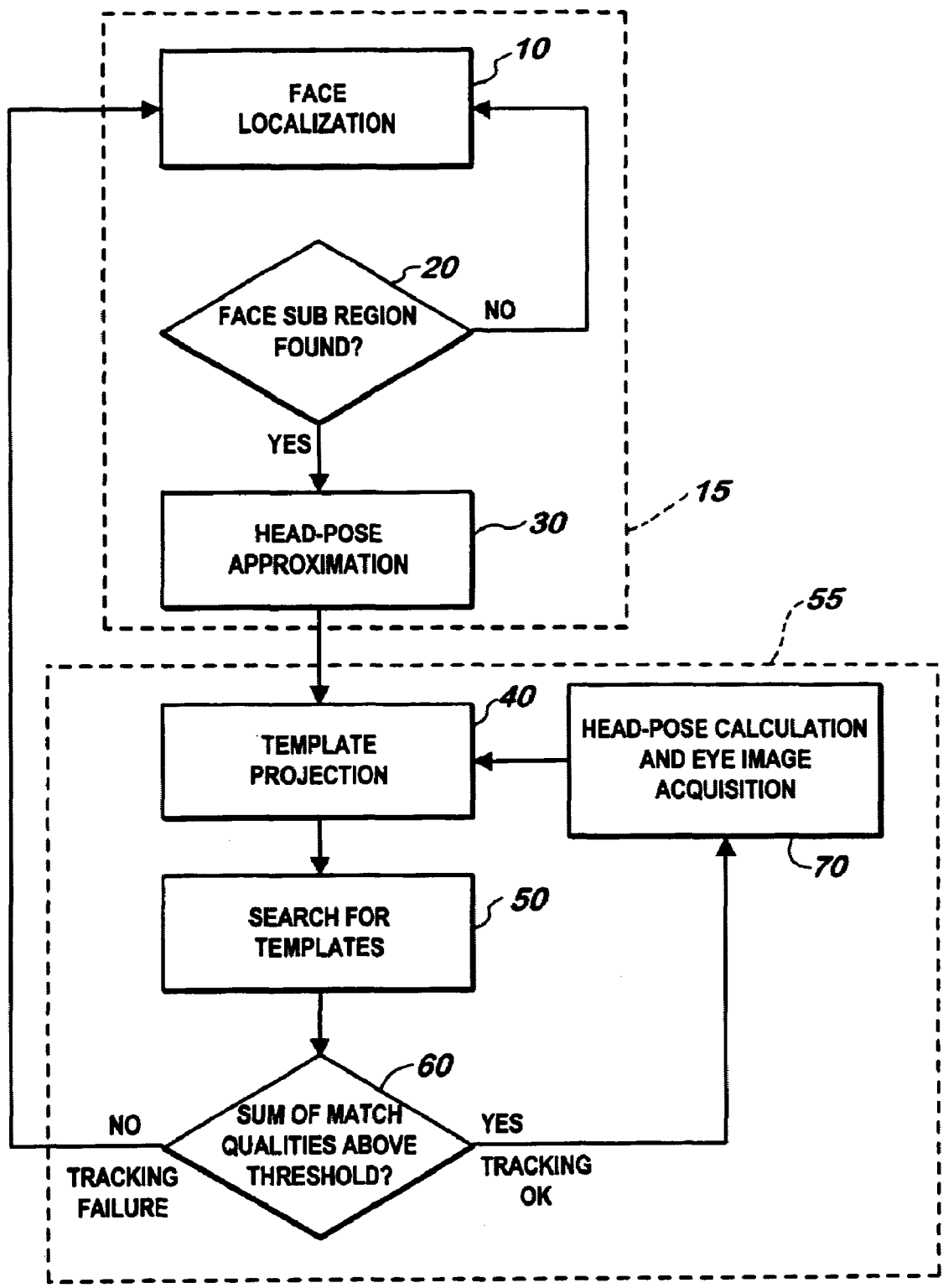
FIG. 1 is a flow chart outlining the head-Pose tracking algorithm according to the present invention.

FIG. 1 shows a flow chart of a method of performing head-pose tracking according to an embodiment of the present invention. The method has two main phases, namely preliminary head pose determination 15 and the head pose tracking loop 55. Each of these phases 15, 55 comprise a number of steps and each of the sub steps can further comprise a number of sub steps.

Preliminary head pose determination 15 includes the steps of face localisation 10 and head pose approximation 30. The head pose tracking loop 55 includes the phases of template projection 40, search for templates 50 and head pose calculation and eye image acquisition 70.

A system capable of performing head tracking will typically comprise two cameras mounted such that both cameras can image the head of the subject being studied. The cameras should be spaced apart from one another to add robustness to the system, in the case of occlusion of the face in one particular direction, and also to allow distances and positions to be more accurately calculated. The cameras should be coupled to a processor capable of storing and/or processing the image data collected by the cameras in order to determine, head pose, eye gaze direction and other attributes as described below.

Turning now to each of the phases in more detail. In order to establish head tracking, either before entering the head pose tracking loop initially, or when recovering from tracking failures, an approximate location of the head within the field of view of at least one camera is determined. This phase is referred to as preliminary head pose determination 15.

The first step to be performed in preliminary head pose determination 15 is face localisation 10. Face localisation 10 is performed by sub-sampling the image taken from the camera, and searching this sub-sampled image for any one a series of low resolution face region templates. Initially one of a series of low resolution face region templates is searched for within the sub sampled image. The search uses a normalised cross-correlation technique to test possible locations of the face-region corresponding to the current template within the sub-sampled image.

The face-region templates can be derived from images taken from the front and left and right sides of the face. The front image of the face is broken into multiple subregions to improve the likelihood of finding a matching template under adverse conditions e.g. under conditions of poor or variable lighting.

Using multiple face-region templates increases the probability of finding the face and improves the tracking loop recovery rate, and thus improves the reliability of the system as a whole. This technique is advantageous for example when the following situations occur:

The face is turned away from the camera;
The face is partially occluded;
The face is unevenly lit, including when the face is brightly lit from one side, to such an extent that the image over part of the face is saturated; or
Bright light is shining directly onto the bottom half of the face, but the top is in shadow (such as when the subject is wearing a hat or using a sun-visor)

The face localisation step 10 is repeated until either a match is made with one of the templates. If none of the templates can be matched to the sub sampled image, face localisation is again attempted on the next image produced by the camera.

If at least one of the face-region templates matches the sub-sampled image with a correlation coefficient that exceeds a predetermined threshold, then the face region is determined to be successfully localised.

Once face localisation has been achieved, an initial head pose approximation is made in step 30 of the method. The initial estimate of head-pose is made based on the particular template that was matched, and it's location within the image. For example, a successful match of the region surrounding the left ear is taken to indicate that the head is turned to the right. Once a suitable head pose estimate is made the estimate can be used to enter into the head-pose tracking loop 55.

The head pose tracking loop 55 is based on matching image regions with a set of predetermined facial feature templates. The system has a set of facial feature templates which are split into two groups, an active subset and an inactive subset. The active subset of templates is maintained by adding or subtracting templates from the active subset templates based a number of criteria including, their expected visibility, the quality of each of each template match with the image, and contribution of the template to the area of the face bounded by the template set. The template selection technique aims to maintain the subset of templates such that the subset will provide faster and more precise head-pose measurement than all other possible subsets.

The first step of the head pose tracking loop 55 is template projection 50. During the template projection step 50 the expected template positions are projected on to the image frames from each camera using a Kalman filtered estimate of head-pose. The expected template positions form the basis for defining a search region in which the template can be searched for in order to achieve accurate feature matching.

The next step in the head pose tracking loop 55 is a search for templates within the search regions defined in step 50 above. A normalised cross correlation is used to search for each template, within the designated search regions of the image from each camera. During any one iteration of the template matching routine only the templates in the active subset are searched for in the video images. The worst performing template ie. the template which has lowest correlation with the image within the search region is removed from the active template subset and replaced with a new template which may be used in the next search iteration for that particular feature. This process is repeated for all the search regions on the face.

If the sum of the correlations for each of the templates is above a predetermined threshold then the head pose tracking is successful. If the sum of the correlations is below a threshold then the head pose tracking loop is left and the whole process begins again. In the event that cross correlation of the template sub-set with the image sub-regions does not find template with a suitable match process returns to its initial condition, at the step of face localisation 10 and begins by searching for sub-regions of the face within one sub-sample video frame.

In the event that head pose tracking is confirmed based on the sum of the cross correlations of the feature templates within the designated search regions, then head pose calculation and eye image acquisition can be performed 70.

The step of head pose calculation and eye image acquisition 70 is performed by determining the three dimensional feature locations of the matched templates within the facial images from the two cameras of the system. From the positions of the individual features the head pose can be determined. Additionally, if the positions of the eyes regions within the images are not determined by a template match in step 50 then the eye region position can be determined by calculation from the position of the matched feature templates.

The steps of template projection 40, searching for templates 50 by cross correlation of each of the templates with image sub-regions followed by head pose calculation and eye image acquisition 70 are repeated throughout the process in order to maintain accurate eye image region determination.

As discussed above head-pose is constructed from measurements of known facial features, such as the corners of the mouth, eyes, nostrils, ears, or any other small recognisable areas on the face. Search areas for each feature are estimated using the head-pose measurement, given either by the face localisation 10 or the previous iteration of the tracking loop 55. Locating small subregions of the images from each camera in which to search for a feature matching a feature template has two main benefits. Firstly, the computation time for each search is greatly reduced, and secondly, false feature matching is prevented.

Each feature is precisely located within its particular search area, using a multi-resolution normalised cross-correlation technique such as that described in *Real Time Correlation-based Stereo: algorithm implementation and application*. Technical Report, INRIA, 1993 by Faugeras, O. et al. The multi-resolution template search technique is a simple two-stage process. First, sub-sampled versions of each feature template are used to find approximate locations of each feature. Secondly, the small image region surrounding the approximate location is then searched using the full resolution feature template. This technique greatly reduces the time to perform the feature search.

If the resulting correlation coefficient is greater than a prescribed threshold, then the feature is found. If the feature is found in two or more images, then the feature's three-dimensional location can be computed.

Figure 2:
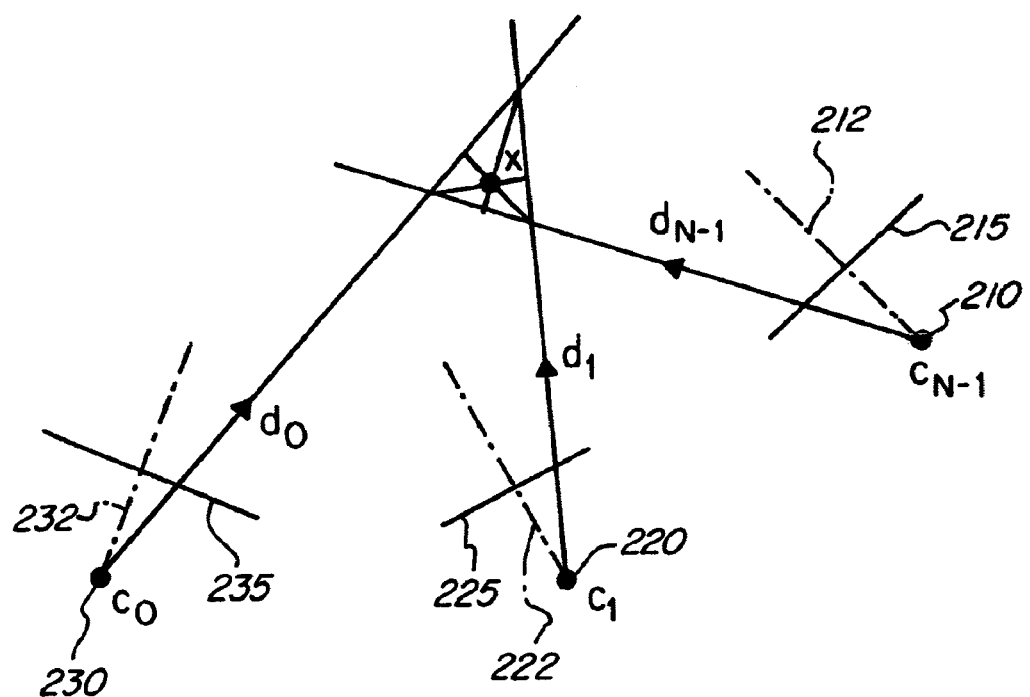
FIG. 2 shows the geometry of template location measurement in three-dimensions.

The three-dimensional position of each feature is measured by determining its location from multiple viewpoints as shown in FIG. 2.

FIG. 2 shows the position of a particular facial feature x and its relative positions with respect to cameras 210, 220, 230. The image plane for each of the cameras 210, 220, 230 are defined by lines 215, 225 and 235 respectively. The system can be generalised to include N cameras, however, for illustration purposes in this embodiment N=3. The points $c_0$ $c_1$ and $c_{N-1}$ represent the centres of the N cameras 210, 220, 230 and lines 212, 222 and 232 represent the normal vectors at the centres $c_0$ $c_1$ and $C_{N-1}$ of cameras 210, 220, 230 respectively. Vectors $d_0$ $d_1$ and $d_{N-1}$ represent the normalised vectors pointing from the centres $C_0$, $C_1$, $C_{n-1}$ of the cameras 210,220 and 230 toward the position of the particular feature of interest x.

To compute the 3D position x of a feature observed by N cameras, we need to solve the equation:

Ax=b where the Matrix A is defined by $$A = \sum_{i=0}^{N-1} (d_i d_i^T - I),$$

and the vector b is defined by $$b = \sum_{i=0}^{N-1} ((c_i^T d_i)d_i - c_i)$$

and I is the identity matrix $$I = \begin{pmatrix} 1 & 0 & 0 \\ 0 & 1 & 0 \\ 0 & 0 & 1 \end{pmatrix}$$

while $c_i$ denotes the centre of the ith camera and $d_i$ is the normalised direction vector pointing from the camera centre $c_i$ towards to feature x observed in the image plane. The 3D position of the feature can then obtained by:

x=A$^{-1}$b

Using the above method, the three dimensional position of a facial feature is determined if it is matched in images from multiple cameras. The facial features that have had their three dimensional position determined in this way are used for head pose determination.

To determine head pose the matched templates are assumed to be connected to a 3D rigid body the rotation and translation required to match this body to a reference 3D body is used to determine the head pose of the person being monitored.

Head pose is determined in three dimensions as a combination of two sets of coordinates rotation (θ, ϕ, φ) and translation (x, y, z). The optimal computed head-pose (consisting of a rotation and a translation components), is that which best maps the head-model to the facial feature three-dimensional measurements. The strength of correlation of each template is used as a weight in a least-squares minimisation procedure. The closed form solution to this problem is biased towards points that are tracking well, making the results robust with respect to occlusion, noise and perspective distortion of features.

The equations of the least-squares closed-form solution to this problem are given below.

The rotation R and translation T of the head model can be recovered by minimising the error E defined by $$E = \sum_{i=0}^{n-1} w_i \|x_i - Rm_i - T\|^2,$$

where $w_i$ is the confidence measurement of the ith feature, $x_i$ is the measured 3D position of the ith feature and $m_i$ is the 3 dimensional position of this feature in the face model.

Using a quaternion representation for the head rotation R, i.e., $$R = \begin{pmatrix} a^2+b^2-c^2-d^2 & 2(bc-ad) & 2(bd+ac) \\ 2(bc+ad) & a^2-b^2+c^2-d^2 & 2(cd-ab) \\ 2(bd-ac) & 2(cd+ab) & a^2-b^2-c^2+d^2 \end{pmatrix},$$

the rotation R can be recovered by minimising the error F using the method of Lagrange, ie.

$$F=2\Sigma w_i(x_i-\bar{x})^T R(m_i-\bar{m}) +\lambda(a^2+b^2+c^2+d^2-1)$$

where $\bar{x}$ is the weighted average of the measurements $x_i$, $\bar{m}$ is the weighted average of the model points $m_i$ and $\lambda$ is the parameter of Lagrange. The translation is then computed using the equation $$T=\bar{x}-R\bar{m}.$$

As described, the head-pose is reconstructed using a set of facial feature templates. To maximise tracking speed and precision, only a subset of the total number of known features is searched for per iteration. A fixed number of templates are added to or removed from the subset at each iteration. The templates in the subset are referred to as "active".

Active template selection is based on:

The quality of the template correlation with the image in the last iteration. (Occluded or distorted facial features should not be searched for).

The distance of the template from the other active templates in the subset. (A larger spread of features across the face produces a more accurate head-pose measurement).

The distortion of the facial feature associated with the template, computed from the head-pose. (Features that are likely to be visible are selected over those that are likely to be occluded).

Kalman filtering is used to smooth the noise in the estimation process, and give a prediction of the head-pose in the next iteration. The Kalman filter uses a constant velocity model for the dynamics of the head-motion. This is a commonly implemented type of Kalman filter. A more detailed description of an implementation of a Kalman filter is given in *Tracking and Data Association*, Volume 179 of Mathematics in Science and Engineering, Academic Press, 1988 by Y. Bar-Shalom and T. E. Fortmann.

Turning now to eye gaze measurement. The eye-gaze estimation technique relies on the measurement of the eyeball centre of rotation, and the centre of the iris. The eye-gaze direction for each eye is computed as the ray passing through these two points. Gaze direction as a whole is then computed as follows:

The visibility of each eye is determined using the head-pose measurement;

When both eyes are visible, the gaze direction is computed as the average direction of both eyes;

When only one eye is visible, the gaze direction is computed using only the visible eye;

When no eyes are visible, the gaze direction is computed as the direction perpendicular to the plane of the face.

Using this technique, the system is able to provide a gracefully degrading estimate of gaze direction, whatever the head-pose.

Thus the key steps in determining eye gaze direction is to determine the positions of the centre of rotation of the eye(s) and to locate the centre of the iris.

Since the eyeball centre is not directly visible, the position of its centre is computed from observations of eye rotation. The system uses a separate calibration process to accurately compute the eyeball centre, for each eye.

When a user is looking directly into the camera lens, the ray from the camera centre to the centre of the iris passes through the eyeball centre of rotation. Using this fact, the system is able to estimate the centre of eyeball rotation by calculating the least-squares intersection of a number of rays.

The calibration procedure requires the person to look straight towards a particular camera for a short period while moving their head around inside the camera's field of view. The system records measurements of head-pose and iris-centre location during this period.

Figure 3:
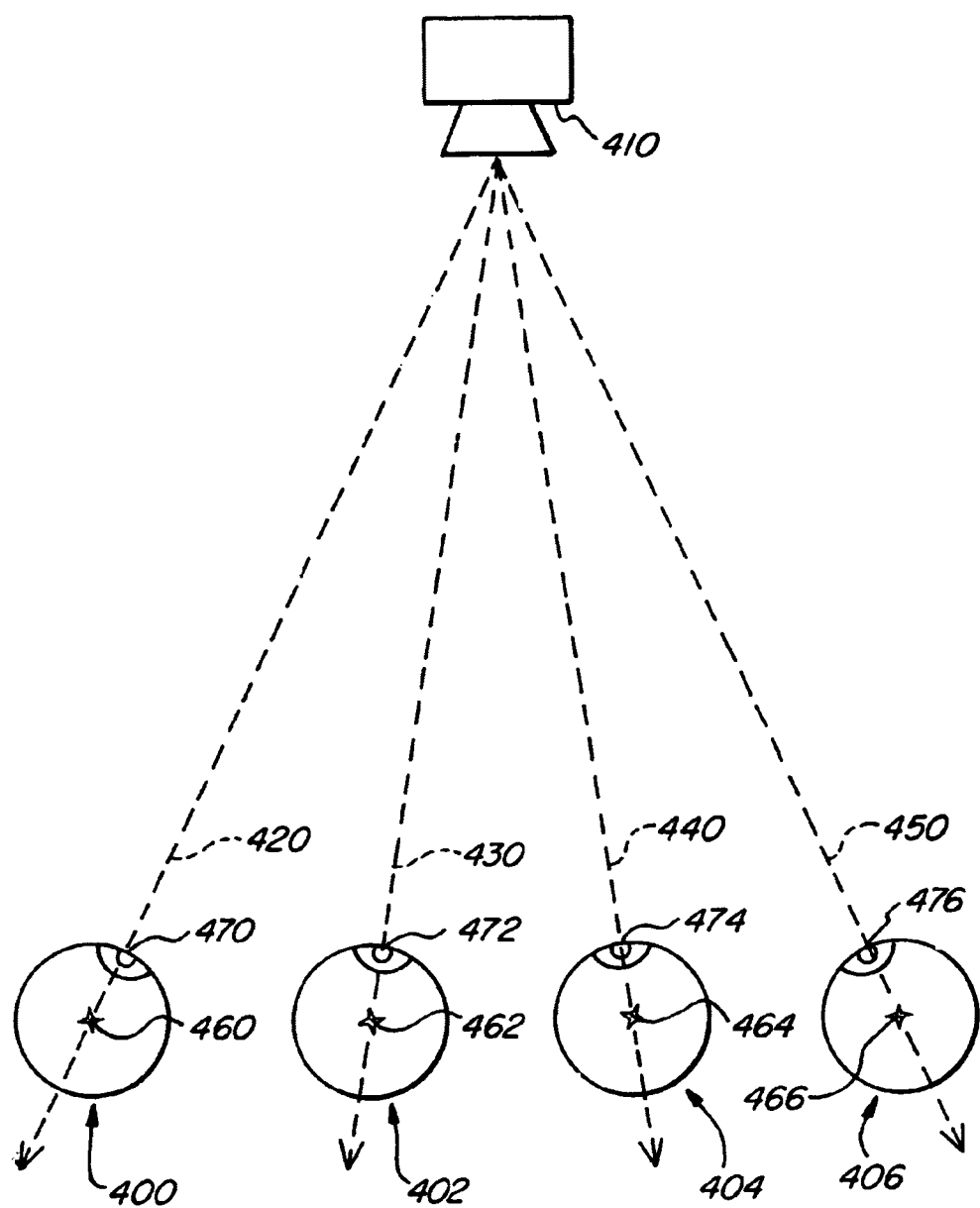
FIG. 3 shows a method of finding the centre of rotation of the eyeball from the frame of reference of the camera.

When the rays are represented in the frame-of-reference of the camera, they all cross the camera centre. FIG. 3 shows a series of eyeballs 400, 402, 404, 406, which represent the eyeball of the user in four different positions relative to a camera 410 during calibration and measurement. A series of rays 420, 430, 440, 450 are shown which pass through the centre of the camera 410, the centres of rotation 460, 462, 464, 466 of each of eyeballs 400, 402, 404, 406 and the centre of the iris 470, 472, 474, 476 of each of eyeballs 400, 402, 404, 406. These rays represent the person looking directly at the camera from various positions.

Figure 4:
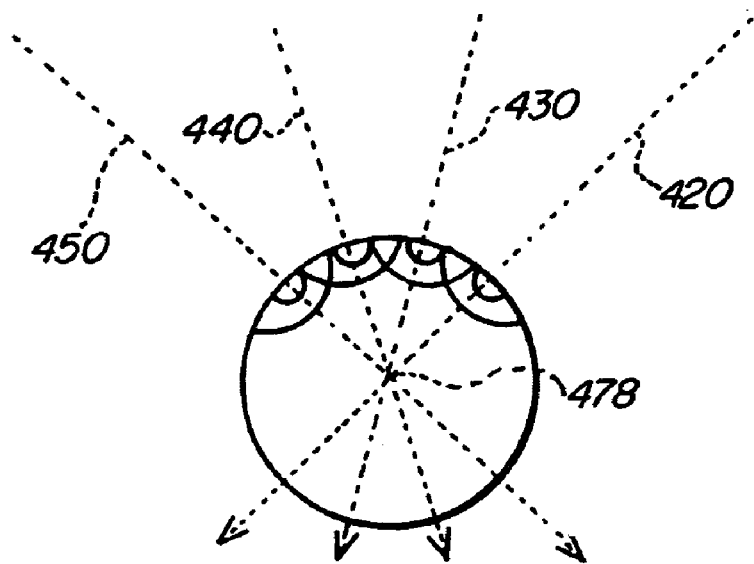
FIG. 4 shows a method of finding the centre of rotation of the eyeball from the frame of reference of the eyeball.

Turning now to FIG. 4, when the rays are represented in the head's frame-of-reference the rays 420, 430, 440, 450 all cross the eyeball centre of rotation 478. Using this geometric property and the position of the eye, which is known from the head-pose measurement process, the system is able to calculate a least-squares estimate of the eyeball centre for each eye.

The calculation is performed for both eyes, and may be improved by using the technique with more than one camera.

The technique clearly relies on determining a 2D position for the iris/pupil centre. However, the calibration technique described could be applied to any system capable of performing 2D pupil centre measurements.

Measurement of the Iris Centre is performed by searching regions around the eye in each image. These regions are determined by the current estimate of head-pose and the model of the face.

The search process includes of the following steps:

Calculating the size of the iris in the image using the head-pose measurement, and the assumption that the iris is a circle with a fixed radius of 6 mm.

Using a circular Hough transform to find a best-fit circular region that is the expected size of the iris. The circular Hough transform process is explained in detail in *Circle Recognition through 2D Hough Transform and Radius Histogramming*, Image and Vision Computing, Volume 17, Pages 15–26, 1999 by D. W. Ioannou and Laine A. Huda.

Figure 5:
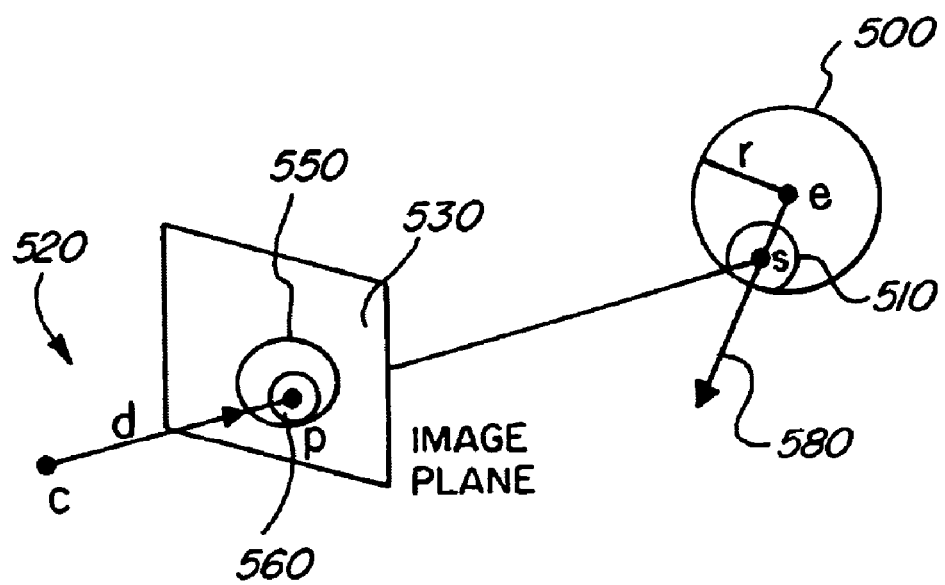
FIG. 5 shows the geometry for the eye gaze measurement method according to an embodiment of the invention.

FIG. 5 shows the a diagram representing the eye gaze measurement calculation. FIG. 5 shows an eyeball 500 of fixed radius r, having an iris 510 with a centre, s and a centre of rotation e. Also shown is schematic representation of a camera 520 showing the centre c and the image plane 530 of the camera 520. The image 550 of the eyeball 500 made in the image plane 530 is also shown. The image 550 of the eyeball 500 also has an iris 560 with a centre p. Vector d represents the ray passing through the centre c of the camera 550, the centre p of the image of the iris 560 and the centre s of the actual iris 510. The vector es 580 represents the vector passing through the centre of rotation e of the eyeball 500 and the centre s of the iris 510 and represents the eye gaze direction. Once the iris or pupil centre and centre of rotation of the eye are determined the eye gaze direction can be computed.

The gaze direction is computed by first computing the 3D position e of the eyeball centre (left or right) by using the relation $$e=Re_m+T,$$

where $e_m$ is the calibrated 3D position of the eyeball centre in the face model, R and T are the recovered rotation and translation of the head using the measurements of the facial features as described above.

Once the centre p of the iris has been located in the image, the direction vector d can be computed pointing from the camera centre c toward the iris centre s. The gaze point is then given by direction of the vector es. The 3D coordinate s can be computed by solving the equation $$s = c - \left( d \cdot \vec{ec} + \sqrt{(d \cdot \vec{ec})^2 - \|\vec{ec}\|^2 + r} \right) d$$

where r denotes the fixed radius of the eyeball.

Figure 6:
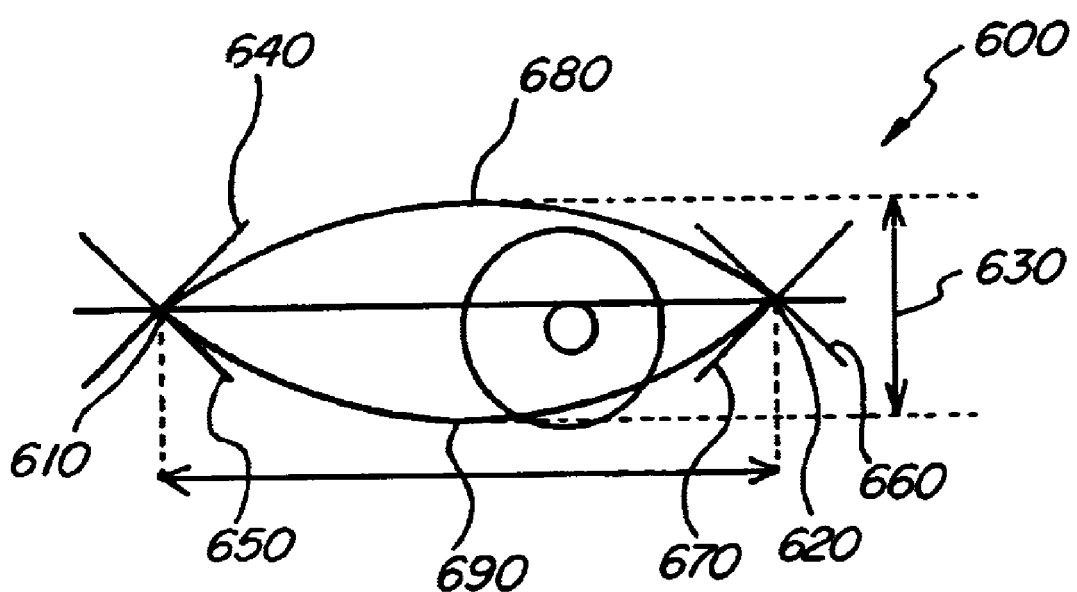
FIG. 6 shows an eye and associated parabolas for applying the eye closure measurement method according to an embodiment of the invention.

A further feature of an embodiment of the present invention is that once an eye position is determined the amount of eye closure may be measured. Eye closure amount is the ratio of the distance between the eyelids to the distance between the eye corners. FIG. 6 shows an image of an eye 600 for the purposes of eye closure measurement.

The three-dimensional location of each eye corner 610, 620 is computed from the head-pose and their position relative to the head. The corners are projected onto the eye image-regions using the camera projective transform.

The distance between the eyelids 630 is determined by the following steps:

1) Applying four oriented edge-detectors 640, 650, 660, 670 on the eye image-region.

2) Determining the two parabolas 680, 690 which best match the edge information calculated in step 1. The edge detectors 640, 650, 660, 670 will typically lie tangential to the parabolas 680, 690. These parabolas 680, 690 always pass through the eye corners.

Once the parabolas 680, 690 are calculated the maximum distance between them is calculated and assumed to be the eye opening amount. The distance between the eye corners is simply the distance between the intersection points of the parabolas 680, 690.

Additionally Blink detection can also be performed. The system detects blink events by combining the output from a number of visual cues. The technique is multi-modal and thus is robust to the failure of an individual method.

FIG. 7 shows a series of 6 graphs showing the 5 individual visual cues which are combined to perform blink detection according to an embodiment. The final graph 7F shows the weighted sum of each of the 5 individual blink detection methods.

Each of the graphs 7A to 7F show the particular value over the same time period, in order to show their correlation.

The blink detection values measured from each eye are weighted and combined according to head-pose, such that the most visible eye receives the greatest weight. This accounts for eye and eyelid distortion due to head-pose and also obscuration by the nose.

The individual visual cues that are measured and used in combination. Graph 7A shows how the eye-template correlation co-efficient changes over time. Eye-template matching is used to compare eye images against templates of the eyes when they are both opened and closed. Before and after a blinking event, the open-eye template will produce a high correlation value, while the closed-eye template will produce a low value. During the blinking event, the opposite is true. Turning now to Graph 7A, the regions 710, 720 may correspond to a change in the correlation co-efficient which may be caused by a blink or other obscuration of the eye.

The temporal sequence of correlation values is convolved with a blink pattern signal template in order to determine whether the obscuration was a blink or due to another obscuration. The output of this convolution constitutes the confidence of the blink event.

Graph 7B shows the number of pixels within the image region with a colour similar to the colour of the sclera of the eye.

The colour distribution of pixels in the eye image regions are used to detect eye-closure amount. When the eye is closed the colour distribution histogram will peak around the skin colour value. When the eye is opened, the colour distribution histogram will contain peaks for the eye sclera, the iris and the skin colour. The troughs at 730 and 740 may correspond to a blink event. Temporal measurement of the height of the peak that relates to the eye-sclera provides a confidence measurement for detecting eye blink events.

Graph 7C shows the rate of change of eye image graphed over time.

The eye-image rate-of-change is measured by temporal image subtraction of one frame from the next. During blinking events there is large rate of change in the eye image region. Thus peaks 750 and 760 may correspond to a blink.

Graph 7D shows the vertical optical flow over the time period of interest. Motion of the upper eyelid during blinking is detected by calculating the vertical optical flow in the eye image region and matching it to an expected signal. Optical flow is a well-known technique used to compute motion in sequence of images. Details of a suitable optical flow calculation are contained in "Determining Optical Flow", Artificial Intelligence Volume 17, p185–204, 1981 by B Horn et al. The sharp transition at 770 between a downward optical flow and upward optical flow is likely to correspond to a blink.

The technique for calculating eye-closure discussed in the previous section also provides information for eye blink detection. Graph 7E shows the change in eye closure amount over the relevant time period. The decrease in the value at 780 should correspond to a blink.

The blink detection method is based on the assumption that a blink consists of both eyes closing and then opening simultaneously. Combining both eye estimates into one value also reduces the probability of a false or missed detection due to partial obscuration of the eyes.

When each of the 5 blink measures is combined in a weighted sum it can be compared with a threshold. A value greater than the threshold is determined to be a blink, a value below is not. Graph 7F shows the weighted sum of Graphs 7A to 7E. Only during region 790 is the threshold level for blink detection, represented by line 795, exceeded.

Thus events represented by graph features 710, 740, 760, 770, 780 is determined to be a blink, whereas events 720, 730 and 750 are not. The event 720 may have been caused by the head tilting or other eye distortion, event 730 could be caused by a partial obscuration of an eye, eg by the nose. A large peak in eye image rate of change, eg 750, could be caused by lighting variations or rapid eye movement.

Flexible feature detection may also be performed by an embodiment of the invention.

Flexible facial features are automatically detected by a stochastic analysis of their position measurements relative to the head-pose, within the face model. Movable facial features, such as the mouth corners, eyebrows, and chin, have a large location measurement variance. This variance is compared to a threshold to determine if the feature can be considered to be flexible.

As will be apparent to the person skilled in the art a system or method according to an embodiment of the present invention will be applicable to a wide range of applications.

Applications

The ability of the embodiments described above to simultaneously detect head-pose and eye-gaze gives rise to a wide range of useful applications. Applications of the invention can be grouped into three broad areas; human-performance measurement, operator monitoring and interactive multimedia.

Such a system can be applied to the study and analysis of people performing tasks. The system can in a passive and non-obtrusive manner observe the patterns of eye-gaze behaviour while a subject is naturally performing a task in a 2 or 3 dimensional work space. Since the invention uses head-pose to estimate eye-gaze a much larger work space coverage of eye-gaze measurement can be achieved, compared with previously known methods. This property makes the system applicable to the evaluation of the ergonomic design of man-machine interfaces for example, the cabin design interior of motor vehicles, cockpits of aeroplanes, and the control panels of equipment used in safety critical systems such as nuclear power plants. Presently, the analysis of ergonomic design is done by firstly recording video images from multiple cameras, sometimes with verbal annotation. The video images are then manually analysed off-line frame by frame to determine the gaze fixation point, the time take to fixate the gaze and the dwell period of fixation. A critical goal of ergonomic design is to create user interface designs that minimise the time to fix the gaze, and the dwell period of gaze fixation. The manual analysis of eye-gaze data is such a time consuming task, that usually only short experiments that are measured in minutes are practically possible. The system described above makes it possible to automatically measure the gaze fixation data; the point, timing and dwell, for experiments conducted over several hours. Additionally this can be done remotely via a network. To assist ergonomic designers the gaze fixation data can be visualised in a 3D graphics environment.

The invention can also be used to monitor the performance of human operators in high work load situations, in order to determine if an operator has become disoriented, inattentive or confused and consequently is making mistakes. Understanding the limits of human performance is vital in safety critical systems such as air traffic control. The invention can be used to find the limits of human performance during the design and implementation of a new system and in real time, during use automatically issue warnings if an operator is approaching his/her performance limit.

The invention also has application in measuring which specific features or events attract a person's visual attention. Applications include measuring what features on a web page or other visual medium, attract a user's gaze, together with the manner in which the user's eyes scan the page. This data will assist designers to construct web page layouts or publications etc that are effective. Similarly, advertising agencies could measure the effectiveness of their promotional material such as television commercials or multimedia presentations. The invention could be used be psychologists and human factor researchers in laboratory experiments that require the measurement of gaze of subjects who are performing specific tasks under varying scenarios.

The invention can also be applied to the measurement of operator inattention and fatigue in safety critical systems such as driving motor vehicles, flying aeroplanes, driving trains or operating equipment. Previously published methods do not simultaneously address the problem of operator inattention and fatigue in realistic real world scenarios. The invention uses a combination of measuring head-pose, eye-gaze, eye-closure, and blink detection to detect both operator inattention and fatigue.

Previous methods rely on head-pose or eye-gaze/blink data to detect either inattention or fatigue. Inattention can be inferred from head-pose data only by using a world model of the work place, and checking whether the head-pose data is directed towards the area of importance or not. While this method can be effective at determining if a driver is looking out of the side window instead of the road ahead, important information about the state of the eyes is not used. A subject may be looking to the side even though the head is facing forward, or in a case of fatigue the eyes could be closed. Previously reported inattention and fatigue systems that rely on eye-gaze/blink detection can only tolerate minimal head movements. In systems that only use eye tracking, natural head movements can cause system failures or false alarms.

The system of an embodiment of the invention performs both head-pose and eye-gaze tracking, thereby continually estimating the subject's eye-gaze whatever the head-pose. For example when a driver is looking ahead towards the cameras the system will have a precise measurement of gaze, if the head is turned towards a side window, the estimate of the eye-gaze will degrade gracefully. When the eyes can not be located, head-pose only is used to estimate the eye-gaze direction. The invention minimises system failures and false detection of inattention or fatigue.

Systems that rely solely on eye tracking methods can not handle the realistic scenario of the subject wearing eyeglasses or sunglasses, since reliable eye tracking is not possible. In this situation the system of an embodiment of the invention relies on head-pose to estimate the eye-gaze direction. The system is able to seamlessly switch between head-pose only and head-pose plus eye-gaze tracking when a subject puts on or removes glasses.

The present system describes eye-closure and blink-detection methods. These two techniques could be used to robustly implement an on-line version of the public-domain drowsy driver detection algorithm called PERCLOS.

An embodiment of the system can be applied as a computer peripheral device to interactive multi-media applications. The system can act as a natural and intuitive input device, augmenting the traditional modes of input such as the mouse and keyboard. The position of the curser can be controlled by eye-gaze, and/or commands can be executed with a nod of the head or the blink of the eye. These attributes coupled with the ability of the invention to track flexible features will allow users to control a wide range of interactive applications. These include; animating computer faces, playing computer and arcade games, low-bandwidth video streaming for teleconferencing, interactive data-casting and operating household appliances.

Presently, computer face animation methods are known that place different coloured markers on the flexible and fixed facial features. Using motion capture technology an animation sequence is recorded, and then analysed off-line. The coloured markers are used to discriminate between the motion of fixed and flexible motion i.e. separate head motion from the motion of facial features such as the lips. A computer model of a face is then animated according to the motion of the markers. The system according to an embodiment can allow the animation process to be at least done in real-time without the need for coloured markers.

In the field of entertainment, a system according to an embodiment of the invention will make the experience of playing computer games highly interactive. Eye-gaze can be used to navigate through the games world, the facial expressions of users captured by the interface could be used to animate virtual characters in the games world which would also interact with other digital characters controlled by other users.

Video streaming for teleconferencing is a high-bandwidth application. The system according to an embodiment could be used to animate a clone of a user at the remote end of the communications link. Rather than transmit large volumes of facial image data, only the motion parameters of the flexible and fixed facial features would be transmitted. Software at the receiver would animate the user's clone accordingly.

Interactive data-casting technology will allow users to select television and entertainment programs on demand, in addition to allowing shopping for products and services, as well as giving access to the Internet. A system according to an embodiment of the invention can provide an intuitive and natural interface to this technology. For instance users could switch between TV programs by fixating their gaze on an icon of the desired product.

In the future household appliances should be become sufficiently intelligent to be controlled by multi-modal inputs, such as the Internet and speech recognition. The ease of use of such appliances will be enhanced by the one application of the system described herein. A user could select which appliance to "talk" to merely by looking at the device in question. For example, a person could just look at the lights and then say "ON!". Additionally, an embodiment of the system could be used to provide intuitive remote control of devices and robotics in hazardous environments, eg in mines, under water or in space thereby providing the context of which device should be operated. An embodiment of the invention could be used together with robotics technology to assist disabled persons to control household devices and appliances or to control motion assistance devices such as wheelchairs. In much the same way as with interactive and virtual reality multimedia, head pose tracking and gaze direction in particular could be used to steer a wheelchair for example. For disabled persons with severely limited or zero movement of their limbs eye-gaze could be used to operate a wide variety of devices.

A computer capable of running any one of the systems disclosed above would typically require the equivalent processing power of two 600 MHz Pentium III processors with 128 Meg of 100 MHz SDRAM. The computer system should have a facility to provide video image capture from two or more video sources, directly to RAM.

Preferably the image sensors should be capable of providing 640×480 pixels of image resolution; at least 256 levels of pixel intensity at a rate of at least 30 frames per second.

The image sensors should be located around the head and pointing towards the face of the person to be monitored.

The system adaptively controls the gain of the image sensor using information obtained from the feature locations on the face that are being tracked. This technique aims to avoiding image saturation at the feature locations and thus reduces the probability of tracking failure due to lighting fluctuation or contrast.

The image sensor gain can be controlled through the adjustment of one or more sensor parameters including, sensor device electronic gain, sensor exposure/sampling period (electronic shutter speed), lens iris mechanical aperture, infra-red filtering and infra-red lighting.

The use of the above parameters to control the image sensors is an advantage over relying on active gain controls in the camera in that the active gain control circuit will not place a priority on the quality of particular regions in the image. The technique for gain control (described above) adjusts the image gain placing priority on factors particularly relevant to the tracking loop.

Other applicable hardware capable of running a system according to an embodiment of the invention will be know to a person skilled in the art.

It will be understood that the invention disclosed and defined herein extends to all alternative combinations of two or more of the individual features mentioned or evident from the text or drawings. All of these different combinations constitute various alternative aspects of the invention.

The foregoing describes embodiments of the present invention and modifications, obvious to those skilled in the art can be made thereto, without departing from the scope of the present invention.

What is claimed is:

1. A method of determining a head-pose measurement of a person, said head pose measurement including a rotational displacement and translation displacement, said method including the steps of:
   (a) capturing images of the face and head of said person from at least two viewpoints;
   (b) computing an initial estimate of head-pose;
   (c) computing the three-dimensional location of two or more facial features; and
   (d) determining a rotational displacement and translation displacement which best match a head-model to the computed location of said two or more facial features.

2. A method of determining a head-pose measurement of a person as claimed in claim 1 wherein step (b) includes the sub-step of, localizing the face within two or more of the captured images.

3. A method of determining a head-pose measurement of a person as claimed in claim 1 wherein step (c) includes the sub-steps of:
   identifying feature search regions, based on said initial estimate of within each captured image that may contain an identifiable facial feature;
   measuring the position of two or more facial features within two or more respective feature search regions in each of said captured images.

4. A method for measuring operator fatigue wherein head-pose is measured using the method of claim 3.

5. A method of animating an image, wherein a head-pose measurement of a person is tracked using a method according to claim 1, and wherein said image is animated in response to said head-pose measurement.

6. A method of passively determining the direction of eye gaze of a person, said method including the steps of:
   (a) capturing images of the face and head of said person from at least two viewpoints;
   (b) localizing the face within two or more of the captured images;
   (c) computing an initial estimate of head-pose;
   (d) identifying feature search regions, based on said initial estimate of head pose, within each captured image that may contain an identifiable facial feature;
   (e) measuring the position of two or more facial features within two or more respective feature search regions in each of said captured images;
   (f) computing the three-dimensional location of each of said two or more facial features;

(g) determining a head pose measurement, said head pose measurement including a rotational displacement and translation displacement which best match a head-model to the computed location of said two or more facial features;

(h) using said head pose measurement to determine the location the centre of one eyeball;

(i) using said head pose measurement to find an eye region corresponding with said eyeball, within each captured image, and determining the location of the centre of the iris of said eye;

(j) using the determined position of said centre of said eyeball and the determined location of the centre of the iris of said eye, to calculate an eye-gaze direction for said eye.

7. A method of passively determining the direction of eye gaze of a person, wherein the direction of eye gaze of said person is calculated by averaging the direction of eye gaze of said person's two eyes, wherein the direction of eye gaze for each eye is determined using the method of claim 6.

8. A method of determining the eye closure amount of an eye located on a person's face, said eye having an eyeball, a top eyelid, and a bottom eyelid, said top and bottom eyelids meeting at a pair of eye corners; wherein eye closure amount is defined as the ratio of eye corner separation to eyelid distance, said method including the steps of:

(a) capturing images of the face and head of said person from at least two viewpoints;

(b) determining a head pose measurement, from said captured images;

(c) using said head pose measurement to determine an eye region within said captured image;

(d) determining the location of said eye corners within said eye region;

(e) fitting at least two oriented edge detectors to said top eyelid and to said bottom eyelid, such that one of said oriented edge detectors of said top eyelid intersects with one oriented edge detectors of said bottom eyelid at each eye corner;

(f) approximating the position of said top eyelid, and said bottom eyelid, by fitting a parabola to said at least two oriented edge detectors corresponding to each eyelid, such that each parabola is tangential to the at least two oriented edge detectors of said parabola's respective eyelid;

(g) determining said eye corner separation by calculating the distance between said eye corners;

(h) determining the maximum eyelid distance by calculating the maximum distance between said parabolas on the portion of said parabolas between said eye corners, in a direction perpendicular to a line joining the eye corners;

(i) calculating the eye closure amount by taking the ratio of the determined eye corner separation to maximum eyelid distance.

9. A method of detecting a blink of a person's eye, said method including the following steps:

calculating eye closure value using a method as claimed in claim 8;

forming a temporal sequence of eye closure values; and comparing said temporal sequence of eye closure values with a blink template, wherein said blink template comprises a sequence of eye closure values corresponding to blink, in order to determine a correlation value between said blink template and said model temporal sequence of eye closure value, wherein a blink is determined to have occurred if said correlation value is greater than a predetermined threshold.

10. A method of detecting a blink of a person's eye using a plurality of independent measurements, wherein each of said plurality of measurements produces a time varying output value, and at least one of said plurality of measurements is a measurement of eye closure value which has been calculated using a method as claimed in claim 8 said method including the step of:

combining the output value of two or more of said plurality of independent measurements in a weighted manner to calculate a blink detection value, wherein a blink is determined to have occurred if said blink detection value is greater than a predetermined threshold blink detection value.

11. A method of detecting a blink of a person's eye as claimed in claim 10 wherein at least one of said plurality of independent measurements is selected from:

an eye region template correlation coefficient;

an optical flow measurement in said eye region;

eye region image rate of change;

color segmentation within the eye region; and iris template correlation coefficient.

12. A method for measuring operator fatigue wherein a blink rate is determined using the method of claim 11.

13. An apparatus when implementing a method of claim 12.

14. A method for measuring operator fatigue wherein eye closure amount is measured using the method of claim 8.

15. A method of determining an eye gaze direction of an observer comprising the steps of:

(a) capturing at least one image of the observer and determining a head pose angle of said observer;

(b) utilizing said head pose angle to locate an expected eye position of said observer; and (c) analyzing said expected eye position to locate at least one eye of said observer and observing the location of the eye to determine an eye gaze direction.

16. A method as claimed in claim 15 wherein said step (a) includes capturing an image in stereo and processing said image in stereo.

17. A method as claimed in claim 16 wherein said step (a) includes the steps of:

(i) determining a set of distinguishable feature locations on an observer's face;

(ii) sorting candidate feature locations of a current head pose to determine a likely head pose.

18. A method as claimed in claim 17 wherein said method degrades gracefully in the presence of occlusion of the observer's face.

19. A method as claimed in claim 18 wherein said occlusion includes the wearing of spectacles or sunglasses by a user.

20. A method as claimed in claim 19 wherein said method further includes determining the three dimensional position of a center of rotation of an observer's eye.

21. A method as claimed in claim 20 wherein said method further determines eye closure and blinking.

22. A method for measuring operator fatigue wherein eye gaze is measured using the method of claim 19.

23. A method of detecting a flexible feature on a person's face, said method including the step of comparing the variance of said feature's position from an expected position of said facial feature, based on a head-pose measurement, with a threshold variance to determine whether the feature is flexible.

24. A method as claimed in claim 23 wherein a head-pose measurement is determined using the method of:
  (a) capturing images of the face and head of said person from at least two viewpoints;
  (b) computing an initial estimate of head pose;
  (c) computing the three dimensional location of two or more facial features; and
  (d) determining a rotational displacement and translation displacement which best matches a head-model to the computed location of said two or more facial features.

25. A method of analysis of a person performing a task wherein the method of claim 24 is used to analyze an action of said person.

26. A method as claimed in claim 23 wherein said method utilizes a measure feature location to determine if individual features on an observer's face are flexible or fixed.

* * * * *